(12) United States Patent
Gaffney et al.

(10) Patent No.: US 7,288,669 B2
(45) Date of Patent: Oct. 30, 2007

(54) NOX TREATED MIXED METAL OXIDE CATALYST

(75) Inventors: Anne Mae Gaffney, West Chester, PA (US); Michele Doreen Heffner, Chalfont, PA (US); Ruozhi Song, Wilmington, DE (US)

(73) Assignee: Rohm and Haas Company, Philadelphia, PA (US)

( * ) Notice: Subject to any disclaimer, the term of this patent is extended or adjusted under 35 U.S.C. 154(b) by 94 days.

(21) Appl. No.: 11/166,293

(22) Filed: Aug. 26, 2005

(65) Prior Publication Data

US 2005/0277547 A1    Dec. 15, 2005

Related U.S. Application Data

(60) Division of application No. 10/731,523, filed on Dec. 9, 2003, now Pat. No. 6,943,145, which is a continuation-in-part of application No. 10/116,241, filed on Apr. 4, 2002, now Pat. No. 6,818,588.

(60) Provisional application No. 60/283,260, filed on Apr. 12, 2001.

(51) Int. Cl.
  *C07C 253/24*  (2006.01)
  *B01J 23/00*  (2006.01)
(52) U.S. Cl. .................. 558/320; 502/312; 562/545
(58) Field of Classification Search .............. 502/311; 558/320; 562/545
  See application file for complete search history.

(56) References Cited

U.S. PATENT DOCUMENTS

| | | | |
|---|---|---|---|
| 5,281,745 | A | 1/1994 | Ushikubo et al. |
| 5,380,933 | A | 1/1995 | Ushikubo et al. |
| 5,472,925 | A | 12/1995 | Ushikubo et al. |
| 6,043,185 | A | 3/2000 | Cirjak et al. |
| 6,080,882 | A | 6/2000 | Midorikawa et al. |

FOREIGN PATENT DOCUMENTS

| | | |
|---|---|---|
| EP | 0 281 280 | 9/1988 |
| EP | 0 630 879 B1 | 12/1994 |
| JP | 7-53448 | 2/1995 |
| JP | 2000-37623 | 2/2000 |
| WO | WO 00/09260 | 2/2000 |
| WO | WO 00/29106 | 5/2000 |

OTHER PUBLICATIONS

Translation of Japanese Laid-Open Patent Application Publication No. 6-228073(Aug. 16, 1994).
Translation of Japanese Laid-Open Patent Application Publication No. 2000-254496(Sep. 19, 2000).

*Primary Examiner*—Kamal A. Saeed

(57) ABSTRACT

An improved catalyst comprising a mixed metal oxide, either promoted or not, is useful for the vapor phase oxidation of an alkane or a mixture of an alkane and an alkene to an unsaturated carboxylic acid and for the vapor phase ammoxidation of an alkane or a mixture of an alkane and an alkene to an unsaturated nitrile.

6 Claims, 1 Drawing Sheet

NOX TREATED MIXED METAL OXIDE CATALYST

CROSS-REFERENCE TO RELATED APPLICATIONS

This non-provisional application is a divisional of non-provisional U.S patent application Ser. No. 10/731,523 filed Dec. 9, 2003 now U.S. Pat. No. 6,943,145, benefit of which is claimed under 35 U.S.C. §120 and which is a continuation-in-part of non-provisional U.S. patent application Ser. No. 10/116,241 filed Apr. 4, 2002, now U.S. Pat. No. 6,818,588, benefit of which is also claimed under 35 U.S.C. §120 and which in turn claims benefit under 35 U.S.C. §119(e) of U.S. provisional Application No, 60/283,260 filed Apr. 12, 2001, priority of which is claimed for the present application.

The present invention relates to improved catalysts for the oxidation of alkanes, or a mixture of alkanes and alkenes, to their corresponding unsaturated carboxylic acids of unsaturated nitriles by vapor phase catalytic oxidation, as well as to a method of making the catalysts. The present invention also relates to a method of producing unsaturated carboxylic acids by subjecting alkanes, or a mixture of alkanes and alkenes, to vapor phase catalytic oxidation in the presence of the improved catalysts. The present invention also relates to a method of producing unsaturated nitriles by subjecting alkanes or a mixture of alkanes and alkenes to vapor phase catalytic oxidation in the presence of ammonia and the improved catalysts.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but, the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

European Published Patent Application No. 0 630 879 B1 discloses a process for producing an unsaturated aldehyde and a carboxylic acid which comprises subjecting propene, isobutene or tertiary butanol to gas phase catalytic oxidation with molecular oxygen in the presence of (i) a catalyst composite oxide represented by the formula

wherein A represents Ni and/or Co, B represents at least one element selected from Mn, Zn, Ca, Mg, Sn and Pb, C represents at least one element selected from P, B, As, Te, W, Sb and Si, and D represents at least one element selected from K, Rb, Cs and Tl; and wherein, when a=12, $0<b\leq10$, $0<c\leq10$, $1\leq d\leq10$, $0\leq e\leq10$, $0\leq f\leq20$ and $0\leq g\leq2$, and x has a value dependent on the oxidation state of the other elements; and (ii) a molybdenum oxide which in itself is substantially inert to said gas phase catalytic oxidation to provide the corresponding unsaturated aldehyde and unsaturated carboxylic acid.

Japanese Laid-Open Patent Application Publication No. 07-053448 discloses the manufacture of acrylic acid by the gas-phase catalytic oxidation of propene in the presence of mixed metal oxides containing Mo, V, Te, O and X wherein X is at least one of Nb, Ta, W, Ti, Al, Zr, Cr, Mn, Fe, Ru, Co, Rh, Ni, Pd, Pt, Sb, Bi, B, In, Li, Na, K, Rb, Cs and Ce.

Published International Application No. WO 00/09260 discloses a catalyst for selective oxidation of propene to acrylic acid and acrolein containing a catalyst composition comprising the elements Mo, V, La, Pd, Nb and X in the following ratio:

wherein X is Cu or Cr or a mixture thereof, a is 1, b is 0.01 to 0.9, c is >0 to 0.2 d is 0.0000001 to 0.2, e is 0 to 0.2, and f is 0 to 0.2; and wherein the numerical values of a, b, c, d, e and f represent the relative gram-atom ratios of the elements Mo, V, La, Pd, Nb and X, respectively, in the catalyst and the elements are present in combination with oxygen.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships:

$0.25<r(Mo)<0.98$, $0.003<r(V)<0.5$, $0.003<r(Te)<0.5$ and $0.003<r(X)<0.5$, wherein r(Mo), r(V), r(Te) and r(X) are the molar fractions of Mo, V, Te and X, respectively, based on the total amount of the essential components exclusive of oxygen.

Published International Application No. WO 00/29106 discloses a catalyst for selective oxidation of propane to oxygenated products including acrylic acid, acrolein and acetic acid, said catalyst system containing a catalyst composition comprising

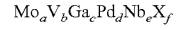

wherein X is at least one element selected from La, Te, Ge, Zn, Si, In and W, a is 1, b is 0.01 to 0.9, c is >0 to 0.2, d is 0.0000001 to 0.2, e is >0 to 0.2, and f is 0.0 to 0.5; and wherein the numerical values of a, b, c, d, e and f represent the relative gram-atom ratios of the elements Mo, V, Ga, Pd, Nb and X, respectively, in the catalyst and the elements are present in combination with oxygen.

Japanese Laid-Open Patent Application Publication No. 2000-037623 discloses a method for producing an unsaturated carboxylic acid comprising subjecting an alkane to a vapor phase catalytic oxidation in the presence of a catalyst having the empirical formula $$Mo_aV_bNb_cX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements.

Nitriles, such as acrylonitrile and methacrylonitrile, have been industrially produced as important intermediates for the preparation of fibers, synthetic resins, synthetic rubbers, and the like. The most popular method for producing such nitriles is to subject an olefin such as propene or isobutene to a catalytic reaction with ammonia and oxygen in the presence of a catalyst in a gaseous phase at a high temperature. Known catalysts for conducting this reaction include a Mo—Bi—P—O catalyst, a V—Sb—O catalyst, a Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula $$Mo_aV_bTe_cX_xO_n$$

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Similarly, Japanese Laid-Open Patent Application Publication No. 6-228073 discloses a method of nitrile preparation comprising reacting an alkane in a gas phase contact reaction with ammonia in the presence of a mixed metal oxide catalyst of the formula $$W_aV_bTe_cX_xO_n$$

wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium and, when a=1, b=0.01 to 1.0, c=0.01 to 1.0, x=0.01 to 1.0 and n is determined by the oxide form of the elements.

U.S. Pat. No. 6,043,185 also discloses a catalyst useful in the manufacture of acrylonitrile or methacrylonitrile by the catalytic reaction in the vapor phase of a paraffin selected from propane and isobutane with molecular oxygen and ammonia by catalytic contact of the reactants in a reaction zone with a catalyst, wherein the catalyst has the empirical formula $$Mo_aV_bSb_cGa_dX_eO_x$$

where X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal and an alkaline earth metal; and when a=1, b=0.0 to 0.99, c=0.01 to 0.9, d=0.01 to 0.5, e=0.0 to 1.0 and x is determined by the oxidation state of the cations present.

Despite the above-noted attempts to provide new and improved catalysts for the oxidation of alkanes to unsaturated carboxylic acids and for the ammoxidation of alkanes to unsaturated nitrites, one impediment to the provision of a commercially viable process for such catalytic oxidations is the identification of a catalyst providing adequate conversion and suitable selectivity, thereby providing sufficient yield of the unsaturated product.

By the present invention, there are provided catalysts wherein the performance is enhanced by treating mixed metal oxide catalyst precursors with a source of $NO_x$ to form a treated admixture, and calcining the treated admixture while the $NO_x$ is present in the admixture. The performance of various types of catalysts may be enhanced by treating mixed metal oxide catalyst precursors, including, but not limited to, mixed metal oxide catalysts and promoted mixed metal oxide catalysts, with a source of $NO_x$.

Thus, in a first aspect, the present invention provides a process for improving the performance characteristics of a catalyst, comprising the steps of:

a) providing precursors for a promoted mixed metal oxide having the empirical formula $$J_jM_mN_nY_yZ_zO_o$$

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements;

b) adding a source of $NO_x$ to said precursors to form an admixture; and c) calcining said admixture while said $NO_x$ is present in said admixture.

In a second aspect, the present invention provides a process for producing an unsaturated carboxylic acid, which comprises subjecting an alkane or a mixture of an alkane and an alkene to a vapor phase catalytic oxidation reaction in the presence of a promoted catalyst containing a mixed metal oxide having the empirical formula $$J_jM_mN_nY_yZ_zO_o$$

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements. The catalyst composition, while in its precursor state, is treated with an $NO_x$ source, such as nitric acid, and calcined.

In a third aspect, the present invention provides a process for producing an unsaturated nitrile, which comprises subjecting an alkane, or a mixture of an alkane and an alkene, and ammonia to a vapor phase catalytic oxidation reaction in the presence of a promoted catalyst containing a mixed metal oxide having the empirical formula

$$J_jM_mN_nY_yZ_zO_o$$

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements. The catalyst composition, while in its precursor state, is treated with an $NO_x$ source, such as nitric acid, and calcined.

In a fourth aspect of the present invention, a promoted catalyst composition is provided containing a mixed metal oxide having the empirical formula

$$J_jM_mN_nY_yZ_zO_o$$

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements. The catalyst composition is treated to exhibit peaks at X-ray diffraction angles (2θ) of 22.1°, 27.1°, 28.2°, 36.2°, 45.2°, and 50.0°, with a relative increase in a diffraction peak at the diffraction angle (2θ) of 27.1 degrees when compared with an untreated catalyst of like empirical formula.

In this regard, in addition to the above noted peak at 27.1 degrees, the preferred mixed metal oxide exhibits the following five main diffraction peaks at specific diffraction angles (2θ) in the X-ray diffraction pattern of the treated mixed metal oxide (as measured using Cu-Kα radiation as the source):

| X-ray lattice plane | | |
|---|---|---|
| Diffraction angle 2θ (±0.3°) | Spacing medium (Å) | Relative Intensity |
| 22.1° | 4.02 | 100 |
| 28.2° | 3.16 | 20~150 |
| 36.2° | 2.48 | 5~60 |
| 45.2° | 2.00 | 2~40 |
| 50.0° | 1.82 | 2~40 |

The intensity of the X-ray diffraction peaks may vary upon the measuring of each crystal. However, the intensity, relative to the peak intensity at 22.1° being 100, is usually within the above-ranges. Generally, the peak intensities at 2θ=22.1° and 28.2° are distinctly observed. However, so long as the above five diffraction peaks are observable, the basic crystal structure is the same even if other peaks are observed in addition to the five diffraction peaks (e.g. at 27.1 degrees), and such a structure is useful for the present invention.

Figure 1:
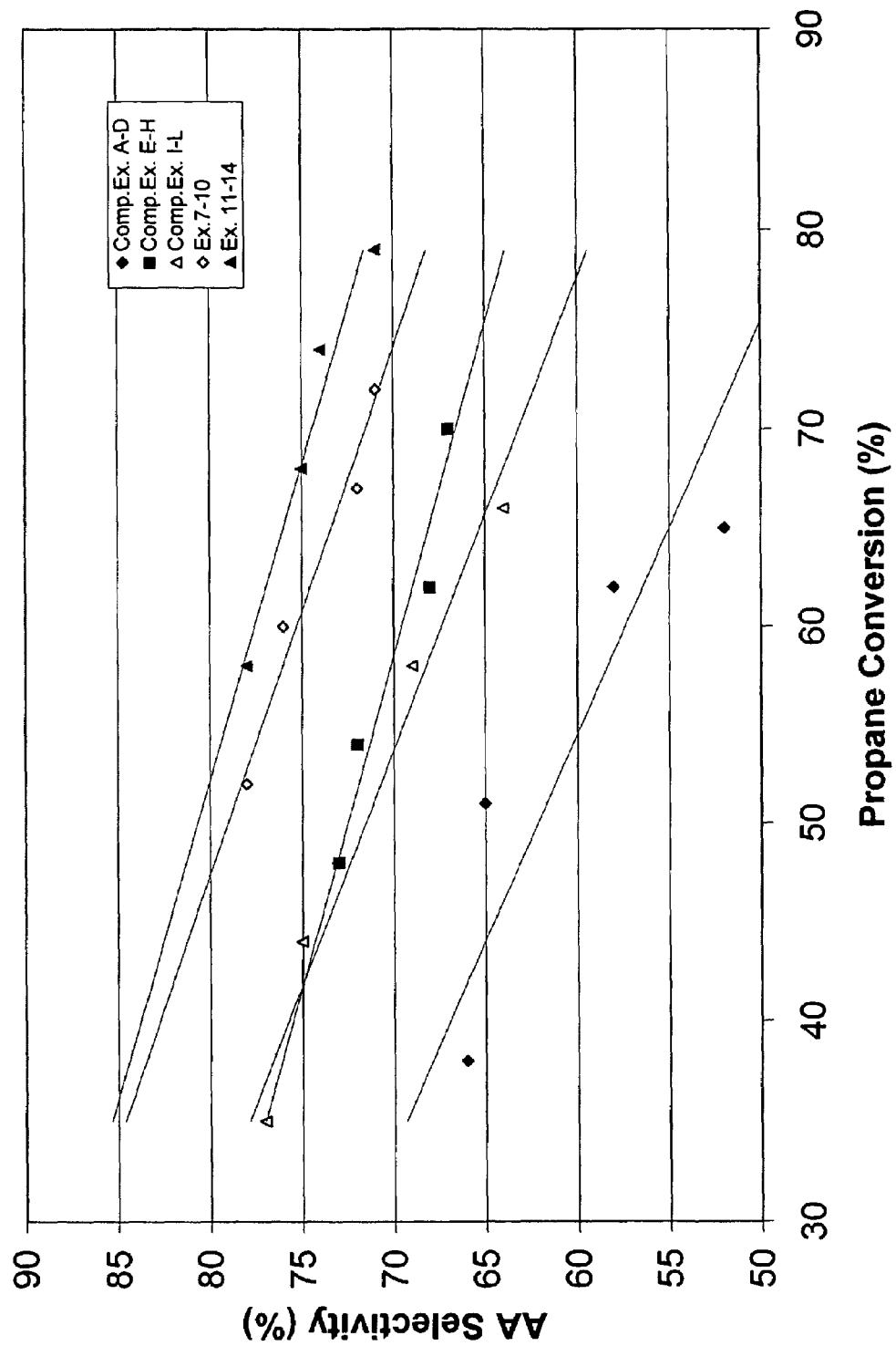
FIG. 1 shows the performance of the catalysts of the Comparative Examples and the Examples of the present invention, in terms of conversion and selectivity, when used to produce acrylic acid from propane.

Turning now in more specific detail to the first aspect of the present invention, the mixed metal oxide is prepared by treating a catalyst precursor admixture with a source of $NO_x$. It will be appreciated that the reference to $NO_x$ herein is intended to cover compounds including nitrogen and oxygen, without limitation as to the specific stoichiometric amounts. However, in a preferred embodiment, x ranges up to 3, and more preferably is an integer selected from 1 or 2.

In a first step, a catalyst precursor admixture may be formed by admixing metal compounds, preferably at least one of which contains oxygen, and at least one solvent, in appropriate amounts to form the admixture, which may be a slurry, solution or combination thereof. A source of $NO_x$ is provided and contacted with at least a portion of the precursor admixture. Liquids are then removed, and the precursor admixture calcined. More specifically, as mentioned, though a slurry may be formed, preferably, a precursor solution is instead formed at this stage of the catalyst preparation.

Where it is desired to make an improved mixed metal oxide catalyst, generally, the metal compounds in the solution will contain elements A, D, E, X and O, such that a mixed metal oxide catalyst precursor will be formed having the empirical formula:

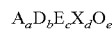
$$A_aD_bE_cX_dO_e$$

wherein A is at least one element selected from the group consisting of Mo and W, D is at least one element selected from the group consisting of V and Ce, E is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Hf, Pb, P, Pm, Eu, Gd, Dy, Ho, Er, Tm, Yb and Lu; and a=1, b=0.01 to 1.0, c=0.01 to 1.0, d=0.01 to 1.0, and e is dependent on the oxidation state of the other elements Where it is desired to make an improved promoted mixed metal oxide catalyst, generally, the metal compounds in the solution will contain elements J, M, N, Y, Z and O, such that a promoted mixed metal oxide catalyst precursor will be formed, as previously defined, i.e., having the empirical formula:

$$J_j M_m N_n Y_y Z_z O_o$$

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements.

It is noted that promoted mixed metal oxides having the empirical formulae $Mo_j V_m Te_n Nb_y Z_z O_o$ or $W_j V_m Te_n Nb_y Z_z O_o$, wherein Z, j, m, n, y, z and o are as previously defined, are particularly suitable for use in connection with the present invention. Additional suitable embodiments are either of the aforesaid empirical formulae, wherein Z is Pd. Suitable solvents for the precursor solution include water; alcohols including , but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. Preferably, though lower concentrations of water are possible for forming a slurry, as stated above, the amount of water is sufficient to ensure an aqueous solution is formed, at the time of mixing.

The precursor admixture is treated with a source of $NO_x$. In a preferred embodiment, the treatment is performed by further admixing the precursor admixture with a fluid for introducing $NO_x$ to the precursor admixture and then drying or calcining the resulting admixture. Accordingly, preferably the fluid includes a $NO_x$ source such as nitric acid, ammonium nitrate, ammonium nitrite, NO, $NO_2$ or a mixture thereof. More preferably, the fluid is a liquid, such as an aqueous solution, including the $NO_x$ source dissolved or dispersed therein. In another embodiment, it is contemplated that a gas including a source of $NO_x$ is bubbled or otherwise introduced into the precursor admixture for treating the admixture. In a highly preferred embodiment, the precursor admixture prior to calcination is prepared by mixing the precursor admixture and nitric acid solution to form a resulting admixture having 0.01 to 20 percent by weight of nitric acid, and more preferably 0.05 to 10 percent by weight of nitric acid. In yet another preferred embodiment, the resulting admixture has 0.1 to 1.5 percent by weight of nitric acid. Alternatively expressed, prior to calcination, preferably the nitric acid is present in an amount of at least 500 ppm of the admixture, more preferably, at least 1500 ppm. An example of a preferred range of concentrations includes 1000 to 15,000 ppm nitric acid.

In another embodiment, where the source of $NO_x$ includes $NO_2$, the amount of $NO_2$ ranges from 500 to 12,000 ppm and more preferably 1000 to 9000 ppm.

By way of example, when a mixed metal oxide of the formula $Mo_a V_b Te_c Nb_d O_e$ (wherein the element A is Mo, the element D is V, the element E is Te and the element X is Nb) is to be prepared, an aqueous solution of niobium oxalate and a solution of aqueous nitric acid may be added to an aqueous solution or slurry of ammonium heptamolybdate, ammonium metavanadate and telluric acid, so that the atomic ratio of the respective metal elements would be in the prescribed proportions. In one specific illustration, it is further contemplated that a 5% aqueous nitric acid is mixed with niobium oxalate solution in a ratio of 1:10 to 1.25:1 parts by volume acid solution to oxalate solution, and more preferably 1:5 to 1:1 parts by volume acid solution to oxalate solution.

For example, when a promoted mixed metal oxide of the formula $Mo_j V_m Te_n Nb_y Au_z O_f$ wherein the element J is Mo, the element M is V, the element N is Te, the element Y is Nb, and the element Z is Au, is to be prepared, an aqueous solution of niobium oxalate may be added to an aqueous solution or slurry of ammonium heptamolybdate, ammonium nietavanadate, telluric acid and ammonium tetrachloroaurate, so that the atomic ratio of the respective metal elements would be in the prescribed proportions.

Once the resulting $NO_x$ treated admixture is formed, the liquid therein is removed by any suitable method, known in the art, for forming a catalyst precursor. Such methods include, without limitation, vacuum drying, freeze drying, spray drying, rotary evaporation and air-drying. Vacuum drying is generally performed at pressures ranging from 10 mm Hg to 500 mm Hg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mm Hg to 760 mm Hg, preferably at a bath temperature of from 40° to 90° C. and at a pressure of from 10 mm Hg to 350 mm Hg, more preferably at a bath temperature of from 40° C. to 60° C. and at a pressure of from 10 mm Hg to 40 mm Hg. Air drying may be effected at temperatures ranging from 25° C. to 90° C. Rotary evaporation or air-drying are generally preferred.

Once obtained, the resulting catalyst precursor is calcined. The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 hr$^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In a preferred mode of operation, the catalyst precursor is calcined in two stages. In the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 700° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination of the mixed metal oxide precursor formulation, a catalyst is formed having the formula $A_aD_bE_cX_dO_e$, wherein A, D, E, X, O, a, b, c, d and e are as previously defined.

Similarly, with calcination of the promoted mixed metal oxide precursor formulation, a promoted catalyst is formed having the formula $J_jM_mN_nY_yZ_zO_o$, wherein J, M, N, Y, Z, O, j, m, n, y, z and o are as previously defined.

The starting materials for the above promoted mixed metal oxide are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylaceton and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

In addition, with reference to the promoter elements for the promoted catalyst, the nickel source may include nickel (II) acetate tetrahydrate, $Ni(NO_3)_2$, nickel(II) oxalate, NiO, $Ni(OH)_2$, $NiCl_2$, $NiBr_2$, nickel(II) acetylacetonate, nickel(II) sulfate, NiS or nickel metal. The palladium source may include $Pd(NO_3)_2$, palladium(II) acetate, palladium oxalate, PdO, $Pd(OH)_2$, $PdCl_2$, palladium acetylacetonate or palladium metal. The copper source may be copper acetate, copper acetate monohydrate, copper acetate hydrate, copper acetylacetonate, copper bromide, copper carbonate, copper chloride, copper chloride dihydrate, copper fluoride, copper formate hydrate, copper gluconate, copper hydroxide, copper iodide, copper methoxide, copper nitrate, copper nitrate hydrate, copper oxide, copper tartrate hydrate or a solution of copper in an aqueous inorganic acid, e.g., nitric acid. The silver source may be silver acetate, silver acetylacetonate, silver benzoate, silver bromide, silver carbonate, silver chloride, silver citrate hydrate, silver fluoride, silver iodide, silver lactate, silver nitrate, silver nitrite, silver oxide, silver phosphate or a solution of silver in an aqueous inorganic acid, e.g., nitric acid. The gold source may be ammonium tetrachloroaurate, gold bromide, gold chloride, gold cyanide, gold hydroxide, gold iodide, gold oxide, gold trichloride acid and gold sulfide.

As discussed previously, without limitation, examples of preferred $NO_x$ sources include nitric acid, ammonium nitrate, ammonium nitrite, NO, $NO_2$ or a mixture thereof.

A mixed metal oxide (promoted or not), thus obtained, exhibits excellent catalytic activities by itself. However, the mixed metal oxide can be converted to a catalyst having higher activities by grinding. There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned promoted mixed metal oxide, the viscosity, the concentration, etc. of the solvent used in the case of wet grinding, or the optimum conditions of the grinding apparatus. However, it is preferred that grinding is conducted until the average particle size of the ground catalyst precursor would usually be at most 20 µm, more preferably at most 5 µm. Improvement in the catalytic performance may occur due to such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where wet grinding is conducted.

The mixed metal oxide (promoted or not) obtained by the above-mentioned method may be used as a final catalyst, but it may further be subjected to heat treatment usually at a temperature of from 200° to 700° C. for from 0.1 to 10 hours.

The resulting mixed metal oxide (promoted or not) may be used by itself as a solid catalyst. It also may be formed into a catalyst with a suitable carrier, such as, without limitation, silica, alumina, titania, aluminosilicate, diatomaceous earth or zirconia, according to art-disclosed techniques. Further, it may be processed to a suitable shape or particle size using art disclosed techniques, depending upon the scale or system of the reactor.

Alternatively, the metal components of the presently contemplated catalyst may be supported on materials such as alumina, silica, silica-alumina, zirconia, titania, etc. by conventional incipient wetness techniques. In one typical method, solutions containing the metals are contacted with the dry support such that the support is wetted; then, the resultant wetted material is dried, for example, at a temperature from room temperature to 200° C. followed by calcination as described above. In another method, metal solutions are contacted with the support, typically in volume ratios of greater than 3:1 (metal solution:support), and the solution agitated such that the metal ions are ion-exchanged onto the support. The metal-containing support is then dried and calcined as detailed above.

Turning now in more specific detail to the second aspect of the present invention, the present invention provides a process for producing an unsaturated carboxylic acid, which comprises subjecting an alkane, or a mixture of an alkane and an alkene ("alkane/alkene"), to a vapor phase catalytic oxidation reaction in the presence of a catalyst containing the above promoted mixed metal oxide, to produce an unsaturated carboxylic acid.

In the production of such an unsaturated carboxylic acid, it is preferred to employ a starting material gas that contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene):(oxygen):(diluting gas):($H_2O$) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{3-8}$ alkane, particularly propane, isobutane or n-butane; more preferably, propane or isobutane; most preferably, propane. According to the present invention, from such an alkane, an unsaturated carboxylic acid such as an α,β-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is preferred to employ a mixture of $C_{3-8}$ alkane and $C_{3-8}$ alkene, particularly propane and propene, isobutane and isobutene or n-butane and n-butene. As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an α,β-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material atkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

The second aspect of the present invention will be described in still further detail with respect to a case where propane is used as the starting material alkane and air is used as the oxygen source. The reaction system may be preferably a fixed bed system. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 hr$^{-1}$, preferably 300 to 6,000 hr$^{-1}$, more preferably 300 to 2,000 hr$^{-1}$; the average contact time with the catalyst can be from 0.01 to 10 seconds or more, but is usually in the range of from 0.1 to 10 seconds, preferably from 0.2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. in such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

Turning now in more specific detail to the third aspect of the present invention, the method of the present invention comprises subjecting an alkane, or a mixture of an alkane and an alkene, to a vapor phase catalytic oxidation reaction with ammonia in the presence of a catalyst containing the above mixed metal oxide, to produce an unsaturated nitrile.

In the production of such an unsaturated nitrile, as the starting material alkane, it is preferred to employ a $C_{3-8}$ alkane such as propane, butane, isobutane, pentane, hexane and heptane. However, in view of the industrial application of nitrites to be produced, it is preferred to employ a lower alkane having 3 or 4 carbon atoms, particularly propane and isobutane.

Similarly, as the starting material mixture of alkane and alkene, it is preferred to employ a mixture of $C_{3-8}$ alkane and $C_{3-8}$ alkene such as propane and propene, butane and butene, isobutane and isobutene, pentane and pentene, hexane and hexene, and heptane and heptene. However, in view of the industrial application of nitrites to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

The third aspect of the present invention will be described in further detail with respect to a case where propane is used as the starting material alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The process of the third aspect of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 hr$^{-1}$, preferably from 300 to 6,000 hr$^{-1}$, more preferably from 300 to 2,000 hr$^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

Turning now in more specific detail to the fourth aspect of the present invention, the treated catalyst exhibits peaks at diffraction angles (2θ) of 22.1°, 27.1°, 28.2°, 36.2°, 45.2°, and 50.0°. As compared with an untreated catalyst composition, the treated catalyst composition of the present invention exhibits an X-ray diffraction pattern having a relative increase in a diffraction peak at a diffraction angle (2θ) of 27.1 degrees when compared with an untreated catalyst, which may exhibit no peak at all at 27.1 degrees.

The relative difference between peak intensities of treated versus untreated compositions may be greater than 5%, more preferably greater than 10%, and still more preferably greater than 20% of the intensity of the untreated catalyst composition at the diffraction angle (2θ) of 27.1 degrees. Without intending to be bound by theory, it is believed that at least two phases (A and B) are present in the resulting mixed metal oxide catalyst and the treatment of the catalyst precursor with a source of NO$_x$ results in an increase in phase B relative to phase A in the resulting catalyst. The increase in phase B is believed to contribute to improved performance of the catalyst in terms of selectivity, reactivity and yield.

EXAMPLES

Catalyst Preparation

Example 1

100 mL of an aqueous solution containing ammonium heptamolybdate tetrahydrate (1.0 M Mo), ammonium metavanadate (0.3 M V) and telluric acid (0.23 M Te), formed by dissolving the corresponding salts in water at 70° C., was added to a 1000 mL rotavap flask. Then 50 mL of an aqueous solution of niobium oxalate (0.25M Nb) and oxalic acid (0.31M) were added thereto. After removing the water via a rotary evaporator with a warm water bath at 50° C. and 28 mm/Hg, the solid materials were further dried in a vacuum oven at 25° C. overnight and then calcined. Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. The final catalyst had a nominal composition of $Mo_1V_{0.3}Te_{0.23}Nb_{0.125}O_f$. The catalyst, thus obtained, was pressed in a mold and then broken and sieved to 10-20 mesh granules for reactor evaluation.

Example 2

100 mL of an aqueous solution containing ammonium heptamolybdate tetrahydrate (1.0 M Mo), ammonium metavanadate (0.3 M V) and telluric acid (0.23 M Te), formed by dissolving the corresponding salts in water at 70° C., was added to a 1000 mL rotavap flask. Then 10 mL of 5% aqueous HNO$_3$ and 50 mL of an aqueous solution of niobium oxalate (0.25 M Nb) and oxalic acid (0.31 M) were added thereto. After removing the water via a rotary evaporator with a warm water bath at 50° C. and 28 mm/Hg, the solid materials were further dried in a vacuum oven at 25° C. overnight and then calcined. Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. The final catalyst had a nominal composition of $Mo_1V_{0.3}Te_{0.23}Nb_{0.125}O_f$. The catalyst, thus obtained, was pressed in a mold and then broken and sieved to 10-20 mesh granules for reactor evaluation.

Example 3

100 mL of an aqueous solution containing ammonium heptamolybdate tetrahydrate (1.0 M Mo), ammonium metavanadate (0.3 M V) and telluric acid (0.23 M Te), formed by dissolving the corresponding salts in water at 70° C., was added to a 1000 mL rotavap flask. Then 20 mL of 5% aqueous HNO$_3$ and 50 mL of an aqueous solution of niobium oxalate (0.25 M Nb) and oxalic acid (0.31 M) were added thereto. After removing the water via a rotary evaporator with a warm water bath at 50° C. and 28 mm/Hg, the solid materials were further dried in a vacuum oven at 25° C. overnight and then calcined. Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. The final catalyst had a nominal composition of $Mo_1V_{0.3}Te_{0.23}Nb_{0.125}O_f$. The catalyst, thus obtained, was pressed in a mold and then broken and sieved to 10-20 mesh granules for reactor evaluation.

Example 4

100 mL of an aqueous solution containing ammonium heptamolybdate tetrahydrate (1.0 M Mo), ammonium metavanadate (0.3 M V) and telluric acid (0.23 M Te), formed by dissolving the corresponding salts in water at 70° C., was added to a 1000 mL rotavap flask. Then 30 mL of 5% aqueous $HNO_3$ and 50 mL of an aqueous solution of niobium oxalate (0.25 M Nb) and oxalic acid (0.31 M) were added thereto. After removing the water via a rotary evaporator with a warm water bath at 50° C. and 28 mm/Hg, the solid materials were further dried in a vacuum oven at 25° C. overnight and then calcined. Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. The final catalyst had a nominal composition of $Mo_1V_{0.3}Te_{0.23}Nb_{0.125}O_f$. The catalyst, thus obtained, was pressed in a mold and then broken and sieved to 10-20 mesh granules for reactor evaluation.

Example 5

100 mL of an aqueous solution containing ammonium heptamolybdate tetrahydrate (1.0 M Mo), ammonium metavanadate (0.3 M V) and telluric acid (0.23 M Te), formed by dissolving the corresponding salts in water at 70° C., was added to a 1000 mL rotavap flask. Then 40 mL of 5% aqueous $HNO_3$ and 50 mL of an aqueous solution of niobium oxalate (0.25 M Nb) and oxalic acid (0.31 M) were added thereto. After removing the water via a rotary evaporator with a warm water bath at 50° C. and 28 mm/Hg, the solid materials were further dried in a vacuum oven at 25° C. overnight and then calcined. Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. The final catalyst had a nominal composition of $Mo_1V_{0.3}Te_{0.23}Nb_{0.125}O_f$. The catalyst, thus obtained, was pressed in a mold and then broken and sieved to 10-20 mesh granules for reactor evaluation.

Example 6

100 mL of an aqueous solution containing ammonium heptamolybdate tetrahydrate (1.0 M Mo), ammonium metavanadate (0.3 M V) and telluric acid (0.23 M Te), formed by dissolving the corresponding salts in water at 70° C., was added to a 1000 ml rotavap flask. Then 50 mL of 5% aqueous $HNO_3$ and 50 mL of an aqueous solution of niobium oxalate (0.25 M Nb) and oxalic acid (0.31 M) were added thereto. After removing the water via a rotary evaporator with a warm water bath at 50° C. and 28 mm/Hg, the solid materials were further dried in a vacuum oven at 25° C. overnight and then calcined. Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours). The final catalyst had a nominal composition of $Mo_1V_{0.3}Te_{0.23}Nb_{0.125}O_f$. The catalyst, thus obtained, was pressed in a mold and then broken and sieved to 10-20 mesh granules for reactor evaluation.

Evaluation and Results

Catalysts were evaluated in a 10 cm long Pyrex tube reactor (internal diameter: 3.9 mm). The catalyst bed (4 cm long) was positioned with glass wool at approximately mid-length in the reactor and was heated with an electric furnace. Mass flow controllers and meters regulated the gas flow rate. The oxidation was conducted using a feed gas stream of propane, steam and air, with a feed ratio of propane:steam:air of 1:3:96. The reactor effluent was analyzed by an FTIR. The results at a 3 second residence time are shown in Table 1.

TABLE 1

| Example | Temp. C. | % C3 Conv. | % AA yield |
|---------|----------|------------|------------|
| 1 | 390 | 41 | 17 |
| 2 | 350 | 63 | 34 |
| 3 | 381 | 46 | 34 |
| 4 | 373 | 55 | 40 |
| 5 | 389 | 56 | 43 |
| 6 | 373 | 48 | 37 |

As gleaned from the above, the present catalyst compositions, when treated according to the present invention performs better than untreated compositions of like empirical formula. The treated catalyst composition exhibits at least 1.5, and more preferably 2, times the yield of reaction product as compared with an untreated catalyst composition of like empirical formula.

A relative improvement in the conversion of the gaseous reactant (e.g., alkane or alkene) of at least 10%, and more preferably at least 20% is observed using the treated composition of the present invention, as compared with an untreated composition under like processing conditions.

Comparative Examples A, B, C & D (Mixed Metal Oxide Catalysts without NOx Treatment)

A catalyst of nominal composition $Mo_{1.0}V_{0.3}Te_{0.23}Nb_{0.17}O_x$ was prepared in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb) and oxalic acide (0.155M) were added thereto. After removing the water via a rotary evaporator with a warm water bath at 50° C. and 28 mm Hg, the solid materials were further dried in a vacuum oven at 25° C. overnight and then calcined.

Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.

The catalyst, thus obtained, was pressed and sieved to 14-20 mesh granules for reactor evaluation. 4 g of these granules were packed into a stainless steel tubular reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography, in an SRI 8610C gas chromatograph, equipped with MS and Porapak Q columns and TCD detector and available from SRI Instruments, to determine the propane conversion. The liquid phase was also analyzed by gas chromatography, in an HP 6890 gas chromatograph equipped with FFAP capillary column and an FID detector and available from Hewlitt-Packard, for the yield of acrylic acid.

The results along with residence time and reactor temperature are shown in Table 2 and FIG. 1.

TABLE 2

| Examples | Residence Time (sec) | Temperature (° C.) | Propane Conversion (%) | Acrylic Acid Selectivity (%) | Acrylic Acid Yield (%) |
|---|---|---|---|---|---|
| Comp. Ex. A | 3 | 380 | 38 | 66 | 25 |
| Comp. Ex. B | 3 | 389 | 51 | 65 | 33 |
| Comp. Ex. C | 3 | 397 | 62 | 58 | 36 |
| Comp. Ex. D | 3 | 399 | 65 | 52 | 34 |

Comparative Examples E, F, G & H (Mixed Metal Oxide Catalysts with NOx Treatment)

A catalyst of nominal composition $Mo_{1.0}V_{0.3}Te_{0.23}Nb_{0.17}O_x$ was prepared in the presence of nitric acid in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined.

Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.

The catalyst, thus obtained, was pressed and sieved to 14-20 mesh granules for reactor evaluation. 4 g of these granules were packed into a stainless steel tubular reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography, in an SRI 8610C gas chromatograph, equipped with MS and Porapak Q columns and TCD detector and available from SRI Instruments, to determine the propane conversion. The liquid phase was also analyzed by gas chromatography, in an HP 6890 gas chromatograph equipped with FFAP capillary column and an FID detector and available from Hewlitt-Packard, for the yield of acrylic acid.

The results along with residence time and reactor temperature are shown in Table 3 and FIG. 1.

TABLE 3

| Examples | Residence Time (sec) | Temperature (° C.) | Propane Conversion (%) | Acrylic Acid Selectivity (%) | Acrylic Acid Yield (%) |
|---|---|---|---|---|---|
| Comp. Ex. E | 3 | 350 | 48 | 73 | 35 |
| Comp. Ex. F | 3 | 358 | 54 | 72 | 39 |
| Comp. Ex. G | 3 | 366 | 62 | 68 | 42 |
| Comp. Ex. H | 3 | 373 | 70 | 67 | 47 |

Comparative Examples I, J, K & L (Pd Promoted Mixed Metal Oxide Catalysts without NOx Treatment)

A catalyst of nominal composition $Mo_{1.0}V_{0.3}Te_{0.23}Nb_{0.17}Pd_{0.01}O_x$ was prepared in the following manner: 200 mL of an aqueous solution containing ammonium heptamolybdate tetrahydrate (1.0M Mo), ammonium metavanadate (0.3M V) and telluric acid (0.23M Te)

formed by dissolving the corresponding salts in water at 70° C., was added to a 2000 mL rotavap flask. Then 200 mL of an aqueous solution of ammonium niobium oxalate (0.17M Nb), oxalic acid (0.155M) and palladium nitrate hydrate (0.01M Pd) were added thereto. After removing the water via a rotary evaporator with a warm water bath at 50° C. and 28 mm Hg, the solid materials were further dried in a vacuum oven at 25° C. overnight and then calcined.

Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The catalyst, thus obtained, was pressed and sieved to 14-20 mesh granules for reactor evaluation. 4 g of these granules were packed into a stainless steel tubular reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography, in an SRI 8610C gas chromatograph, equipped with MS and Porapak Q columns and TCD detector and available from SRI Instruments, to determine the propane conversion. The liquid phase was also analyzed by gas chromatography, in an HP 6890 gas chromatograph equipped with FFAP capillary column and an FID detector and available from Hewlitt-Packard, for the yield of acrylic acid.

The results along with residence time and reactor temperature are shown in Table 4 and FIG. 1.

aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.01M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined.

Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. The catalyst, thus obtained, was pressed and sieved to 14-20 mesh granules for reactor evaluation. 4 g of these granules were packed into a stainless steel tubular reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography, in an SRI 8610C gas chromatograph, equipped with MS and Porapak Q columns and TCD detector and available from SRI Instruments, to determine the propane conversion. The liquid phase was also

TABLE 4

| Examples | Residence Time (sec) | Temperature (° C.) | Propane Conversion (%) | Acrylic Acid Selectivity (%) | Acrylic Acid Yield (%) |
|---|---|---|---|---|---|
| Comp. Ex. I | 3 | 342 | 35 | 77 | 27 |
| Comp. Ex. J | 3 | 356 | 44 | 75 | 33 |
| Comp. Ex. K | 3 | 372 | 58 | 69 | 40 |
| Comp. Ex. L | 3 | 382 | 66 | 64 | 42 |

Examples 7-10

(Pd Promoted Mixed Metal Oxide Catalysts with NOx Treatment)

A catalyst of nominal composition $Mo_{1.0}V_{0.3}Te_{0.23}Nb_{0.17}Pd_{0.01}O_x$ was prepared in the presence of nitric acid in the following manner: 200 mL of an analyzed by gas chromatography, in an HP 6890 gas chromatograph equipped with FFAP capillary column and an FID detector and available from Hewlitt-Packard, for the yield of acrylic acid.

The results along with residence time and reactor temperature are shown in Table 5 and FIG. 1.

TABLE 5

| Examples | Residence Time (sec) | Temperature (° C.) | Propane Conversion (%) | Acrylic Acid Selectivity (%) | Acrylic Acid Yield (%) |
|---|---|---|---|---|---|
| Ex. 7 | 3 | 357 | 52 | 78 | 41 |
| Ex. 8 | 3 | 361 | 60 | 76 | 46 |
| Ex. 9 | 3 | 369 | 67 | 72 | 48 |
| Ex. 10 | 3 | 377 | 72 | 71 | 51 |

Examples 11-14

(Pd Promoted Mixed Metal Oxide Catalysts with NOx Treatment and Oxalic Acid Extraction)

A catalyst of nominal composition $Mo_{1.0}V_{0.3}Te_{0.23}Nb_{0.17}Pd_{0.01}O_x$ was prepared in the presence of nitric acid and extracted with oxalic acid in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.01M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined.

Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. 30 g of the solid materials were ground and added to 100 mL solution of 30% oxalic acid in water. The resulting suspension was stirred at 125° C. for 5 hrs in a Parr reactor, then the solids were collected by gravity filtration and dried in a vacuum oven overnight at 25° C. The catalyst, thus obtained, was pressed and sieved to 14-20 mesh granules for reactor evaluation. 4 g of these granules were packed into a stainless steel tubular reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography, in an SRI 8610C gas chromatograph, equipped with MS and Porapak Q columns and TCD detector and available from SRI Instruments, to determine the propane conversion. The liquid phase was also analyzed by gas chromatography, in an HP 6890 gas chromatograph equipped with FFAP capillary column and an FID detector and available from Hewlitt-Packard, for the yield of acrylic acid.

The results along with residence time and reactor temperature are shown in Table 6 and FIG. 1.

TABLE 6

| Examples | Residence Time (sec) | Temperature (° C.) | Propane Conversion (%) | Acrylic Acid Selectivity (%) | Acrylic Acid Yield (%) |
|---|---|---|---|---|---|
| Ex. 11 | 3 | 333 | 58 | 78 | 45 |
| Ex. 12 | 3 | 342 | 68 | 75 | 51 |
| Ex. 13 | 3 | 347 | 74 | 74 | 55 |
| Ex. 14 | 3 | 350 | 79 | 71 | 56 |

As gleaned from Comparative Examples A-L and Examples 7-14, the present promoted catalyst compositions, when treated according to the present invention, i.e., with a source of NOx, performs better than untreated catalyst compositions of like empirical formula. In particular, it can be seen from the data of Tables 2-6 and FIG. 1 that, at a given propane conversion rate, the treated promoted catalyst compositions exhibit up to 10% greater AA selectivity as compared with untreated unpromoted and promoted catalyst compositions of like empirical formula. Also, at a given propane conversion rate, the data of tables 2-6 show that the AA yield of the treated promoted catalyst compositions is increased by at least a few percent as compared with untreated unpromoted and promoted catalyst compositions of like empirical formula.

All publications discussed in the foregoing are hereby expressly incorporated by reference herein for all purposes. Catalysts disclosed therein may also be treated using the techniques of the present invention.

What is claimed is:

1. A process for producing an unsaturated carboxylic acid, which comprises subjecting an alkane or a mixture of an alkane and an alkene to a vapor phase catalytic oxidation reaction in the presence of a catalyst containing a mixed metal oxide having the empirical formula $$J_j M_m N_n Y_y Z_z O_o$$

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements, said catalyst composition having been formed from calcining an admixture including catalyst precursors and a source of $NO_x$ for improving catalytic performance.

2. The process according to claim 1, wherein said source of $NO_x$ is selected from nitric acid, ammonium nitrate, ammonium nitrite, NO, $NO_2$ or a mixture thereof.

3. The process according to claim 1, wherein said source of $NO_x$ is nitric acid.

4. A process for producing an unsaturated nitrile, which comprises subjecting an alkane, or a mixture of an alkane and an alkene, and ammonia to a vapor phase catalytic oxidation reaction in the presence of a catalyst containing a mixed metal oxide having the empirical formula $$J_j M_m N_n Y_y Z_z O_o$$

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements, said catalyst composition having been formed from calcining an admixture including catalyst precursors and a source of $NO_x$ for improving catalytic performance.

5. The process according to claim 4, wherein said source of $NO_x$ is selected from nitric acid, ammonium nitrate, ammonium nitrite, NO, $NO_2$ or a mixture thereof.

6. The process according to claim 4, wherein said source of $NO_x$ is nitric acid.

* * * * *